(12) United States Patent
Putman et al.

(10) Patent No.: US 6,681,617 B1
(45) Date of Patent: Jan. 27, 2004

(54) VARIABLE ECCENTRIC RHEOMETER SYSTEM

(75) Inventors: John B. Putman, Cuyahoga Falls, OH (US); Bradley J. Henry, Cuyahoga Falls, OH (US); Joseph G. Bulman, Kent, OH (US)

(73) Assignee: Tech Pro, Inc., Cuyahoga Falls, OH (US)

( * ) Notice: Subject to any disclaimer, the term of this patent is extended or adjusted under 35 U.S.C. 154(b) by 0 days.

(21) Appl. No.: 10/437,642

(22) Filed: May 14, 2003

(51) Int. Cl.[7] ............................................... G01N 11/10
(52) U.S. Cl. ..................................................... 73/54.27
(58) Field of Search .............................. 73/54.27, 54.28, 73/54.39, 794, 811, 843; 374/48; 700/198; 702/43

(56) References Cited

U.S. PATENT DOCUMENTS

| | | | | |
|---|---|---|---|---|
| 3,182,494 A | * | 5/1965 | Beatty et al. ................. | 374/48 |
| 3,538,758 A | * | 11/1970 | Karper et al. ................. | 73/794 |
| 3,581,558 A | * | 6/1971 | Porter et al. .................. | 73/811 |
| 4,546,438 A | * | 10/1985 | Prewitt et al. ............... | 700/198 |
| 4,643,020 A | * | 2/1987 | Heinz ........................ | 73/54.27 |
| 4,794,788 A | * | 1/1989 | Masters et al. ............. | 73/54.27 |
| 5,113,353 A | * | 5/1992 | George ........................ | 702/43 |
| 5,481,903 A | * | 1/1996 | King et al. ................. | 73/54.28 |
| 5,526,693 A | * | 6/1996 | Wise ........................... | 73/843 |
| 6,523,397 B1 | * | 2/2003 | Tosaki ....................... | 73/54.39 |

* cited by examiner

*Primary Examiner*—Hezron Williams
*Assistant Examiner*—J L Politzer
(74) *Attorney, Agent, or Firm*—Renner, Kenner, Greive, Bobak, Taylor & Weber

(57) ABSTRACT

An apparatus for testing polymeric samples is shown in which a polymer specimen is subjected to sinusoidal, oscillatory motion. The oscillatory motion is generated by the use of a continuously variable eccentric cam that is affixed to a drive shaft rotated by a motor. The amplitude of oscillation is determined by the eccentricity of the cam, and verified by measurement of angular deflection. The eccentricity of the cam can be altered, in one embodiment, through the manual manipulation of an adjustable nut, and, in another, automated embodiment, through the motion of the rotating motor. The eccentricity of the cam is continuously variable and can quickly be changed within a single test.

8 Claims, 5 Drawing Sheets

VARIABLE ECCENTRIC RHEOMETER SYSTEM

BACKGROUND OF THE INVENTION

The present invention generally resides in the art of rheometer systems for testing polymers. More particularly, the present invention relates to a variable eccentric cam that is incorporated into to a rheometer system for converting rotary motion at a motor-driven drive shaft into oscillatory motion at a polymer sample die.

Polymers are most often tested according to one of five ASTM methods, namely, ASTM D1646, D2084, D5289, D6204 and D6601. Method D1646 describes the use of a shearing disk viscometer to measure the viscosity and scorch characteristics of a polymer. In this method a rotor continuously rotates, as opposed to oscillating. The second method, D2084, describes a curemeter utilizing an oscillating rotor. The degree of oscillation is fixed and determines the percent strain, such that the device employed is a constant strain instrument. Method D 5289 describes three rotorless curemeter systems wherein one die is oscillated at a fixed amplitude. As in the methods previously discussed, this amplitude is fixed, and the instrument is, therefore, a fixed strain instrument. The present invention is concerned with oscillating instruments, and may be applied to oscillating test instruments currently known or to oscillating test instruments developed in the future, when the test instrument is suitable for the incorporation of the teachings herein.

Several patents describe instruments operating in accordance with ASTM D2084 and D5289. U.S. Pat. No. 3,681,980 illustrates the application of a fixed eccentric cam to facilitate oscillation of a rotor. This amplitude of oscillation is determined by the position of the pin on the eccentric. U.S. Pat. No. 4,794,788 also describes the use of an eccentric to facilitate oscillatory motion. The amplitude of oscillation for these instruments has been fixed for any given test, although the amplitude of oscillation can be changed between tests by changing the position of the pin on the eccentric or by changing the eccentric to one with a different off-set. The structure of such an eccentric cam is shown in FIGS. 1 and 2.

In FIG. 1, it can be seen how the operation of a rotating eccentric cam 100 can convert rotary motion (represented by arrow R) at eccentric cam 100 into oscillatory motion (represented by arrow O) at a polymer sample die 102. A pin 104 extends from eccentric cam 100 to connect to a first end of an eccentric arm 106. The second end of eccentric arm 106 attaches to the first end of the drive plate 108, which has its second end rigidly fixed to die shaft 110. Pin 104 is placed off center on eccentric cam 100 such that, as eccentric cam 100 is rotated by a drive shaft and motor (not shown) pin 104 rotates about the central axis of rotation of eccentric cam 100. It will be appreciated that this causes eccentric arm 106 to be alternatively pushed and pulled by the rotation of eccentric cam 100, such that drive plate 108 is also pushed in and pulled to create oscillation at die shaft 110 and die 102.

In order to achieve different amplitudes of oscillation, eccentric cam 100 might be designed as shown in FIG. 2, wherein eccentric cam 100 provides for three pin positions 104A, 104B and 104C. Each pin position 104A, B, C represents a different amplitude of oscillation, and, thus, the amplitude of oscillation may be changed between tests by changing the position of eccentric arm 106 on the eccentric cam 100 (i.e., by moving the connection of eccentric arm 106 to a new position on eccentric cam 100). While FIG. 2 shows one eccentric cam with three pin positions 104A, B, C, it should be appreciated that, rather than providing multiple pin positions on one eccentric cam 100, multiple eccentric cams 100 might be provided, each with a single pin position 104 placed at a different distance from the center axis of rotation of the eccentric cam 100. In such a case, the eccentric cam would need to be changed between tests in order to provide for differing amplitudes of oscillation.

ASTM D6204 describes the use of a constant strain test, and also discloses the capability of performing a variable strain test. ASTM D6601 fully describes the conditions for evaluating a specimen at more than one strain amplitude during a single test. In this method, a specimen is subjected to strains of 1, 2, 5, 10 and 20% during the same test. In order to use the previous apparatus as shown in FIG. 1, the test must be momentarily stopped while the strain amplitude is manually changed by either (1) changing the position of the eccentric arm on one eccentric cam (when the eccentric provides multiple pin position, as in FIG. 2), or (2) changing the eccentric cam itself (when multiple eccentrics are available having only one pin position).

In the case of (1) above, it would be difficult, if not impossible to have one eccentric with the eccentric positions necessary to achieve 1, 2, 5, 10 and 20% strain. In order to obtain these strain amplitudes for a typical rheometer geometry, the pin positions on the eccentric cam would need to be located at approximately 0.004, 0.009, 0.021, 0.043 and 0.086 inches from the center axis of rotation of the eccentric cam. Even using an eccentric pin as small as 0.125 inches, it would be nearly impossible to accurately machine these positions on one eccentric cam, along a single radius (as in FIG. 2). Even if the positions were machined on the eccentric such that they did not align along a single radius, they would have to be very accurately placed, and some means would need to be provided for distinguishing between each position.

In example (2) above, exchanging eccentric cams to obtain different strains also makes it difficult to achieve all of the strains described in ASTM D6601. In this situation, the test would have to be momentarily stopped while the eccentric cam has changed. However, the procedures require that individual eccentric cams be calibrated, and such calibration would be tedious and time consuming, since five different eccentric cams would be needed. Calibration is critical since the position of the eccentric pin determines where the amplitude crosses through zero amplitude.

To avoid the problems associated with either changing eccentric pin locations or changing eccentric cams, the current apparatus to test according to ASTM D6204 and D6601 are direct drive instruments as described in U.S. Pat. No. 5,079,956. The direct drive system is illustrated in FIG. 3. Therein, a motor 200 is programmed to oscillate, and it is directly fixed to polymer sample die 202 through a die shaft 204, such that the oscillatory motion of motor 200 is directly transferred to die 202. While these direct drive systems are easily calibrated, and allow for fast and automated changing of the oscillation amplitude, they suffer from the fact that continuously testing at small amplitudes can cause excessive wear on the motor and premature failure. In addition, the motor must be very precise in order to provide control at small amplitudes.

Thus, while the prior art has provided some means for converting rotary motion into differing amplitudes of oscillation, there exists a need in the art for a variable eccentric cam that can provide for virtually any desired amplitude of oscillation without necessitating that eccentric cams be changed or requiring that discrete positions for the attachment of the eccentric arm to the eccentric cam be chosen.

SUMMARY OF THE INVENTION

In general, the present invention provides an eccentric cam for use in oscillating rheometer systems wherein the eccentric cam is mounted on a drive shaft and attaches to an eccentric arm for converting rotary motion of the drive shaft into oscillatory motion at a rubber specimen die, which is operatively connected to the eccentric arm through a drive arm. The eccentric cam includes a slide housing that is operatively connected to the drive shaft to rotate therewith such that the slide housing has a center axis of rotation. A slide screw is mounted in the slide housing, and a slide is threaded on the slide screw. The slide includes a connector for attachment to the eccentric arm, and a means is provided for rotating the slide screw to move the slide and thereby change the position of the connector relative to the center axis of rotation of the slide housing. In one particular embodiment, the means for rotating the slide screw is an adjustment nut for manually turning the slide screw to move the slide threaded thereon. In another embodiment, the means for rotating the slide screw includes a screw actuating bevel gear and stationary bevel gear that selectively engages the screw actuating bevel gear.

The eccentric cam is to be employed in a rheometer system, such that the present invention further provides a variable eccentric rheometer system that includes a rotary drive shaft; a slide housing operatively connected to the rotary drive shaft to rotate therewith, such that the slide housing has a center axis of rotation; a slide screw mounted in the slide housing; a slide threaded on the slide screw and including a connecter; means for rotating the slide screw to move the slide and thereby change the position of the connector relative to the center axis of rotation of the slide housing; and eccentric arm having a first end and a second end, wherein the first end of the eccentric arm is fixed to the connector of the slide by a bearing; a drive plate having a first end and second end, wherein the first end of the drive plate is fixed to the second end of the eccentric of the eccentric arm; a die shaft having a first end and a second end, wherein the first end of the die shaft is rigidly fixed to the second tend of the drive plate; and a die rigidly fixed to the second end of the die shaft.

As mentioned, rotation of the slide screw causes the slide to move, which, in turn, changes the position of the connector relative to the center axis of rotation of slide housing. It is the relation of the connector to the center axis of rotation that dictates the amplitude of oscillation, and, thus, the present invention provides an eccentric cam for use in a rheometer system that is continuously variable with respect to the amplitudes of oscillation that it can bring about. In less preferred embodiments, the means of rotating the slide screw is manual, while, in more preferred embodiments, an automated means is provided for accurately achieving the desired amplitude of oscillation at the die.

BRIEF DESCRIPTION OF THE DRAWINGS

For a complete understanding of the objects, techniques and structure of the invention, reference should be made to the following detailed description and accompanying drawings wherein.

PREFERRED EMBODIMENT FOR CARRYING OUT THE INVENTION

Figure 1:
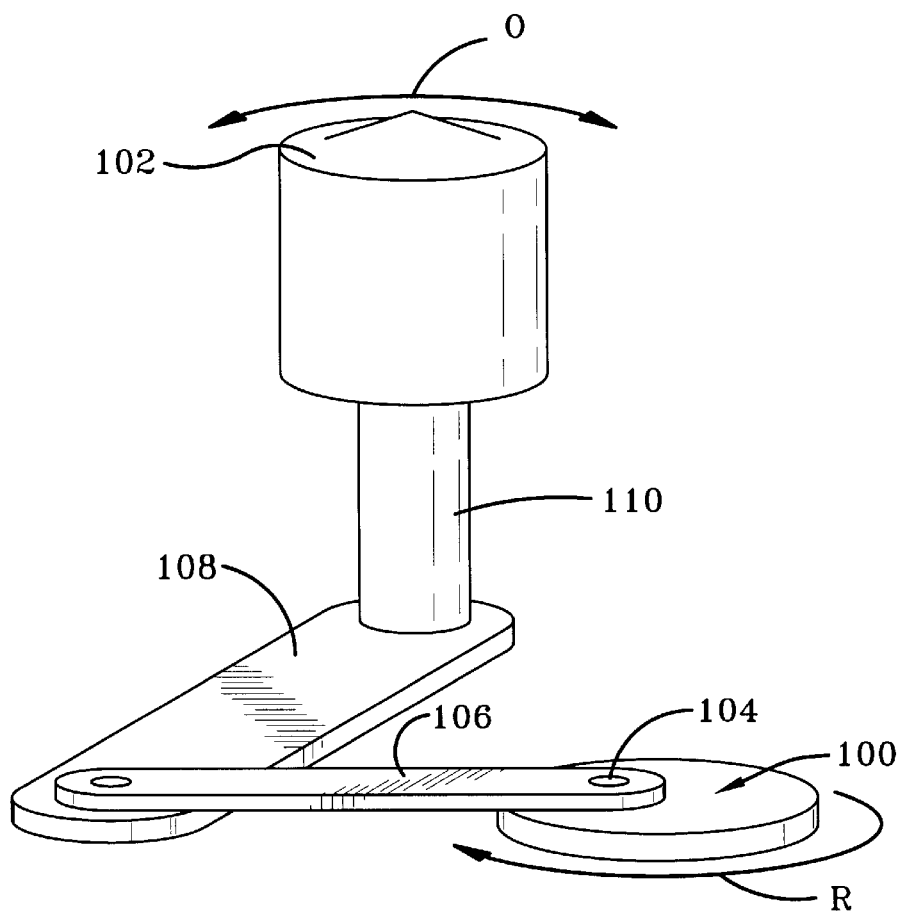
FIG. 1 generally represents a fixed eccentric rheometer system according to the prior art.
Figure 2:
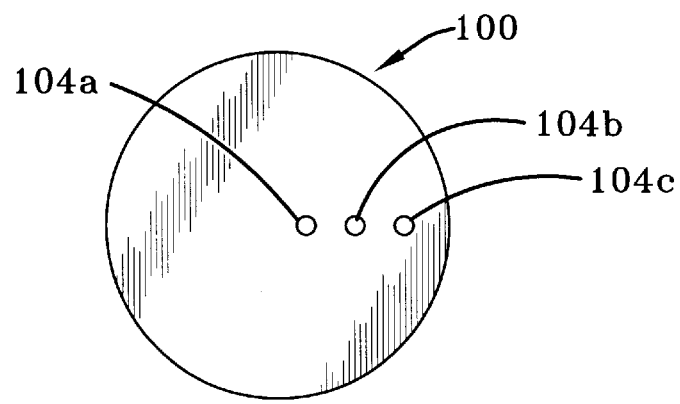
FIG. 2 is a top plan view of a prior art eccentric cam showing three discrete positions for connections to an eccentric arm.
Figure 3:
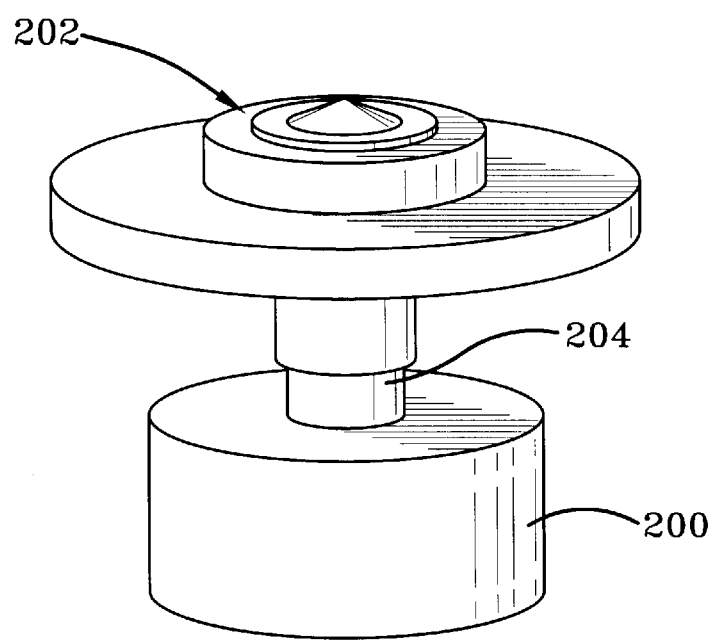
FIG. 3 is a prior art direct drive system of the prior art.
Figure 4:
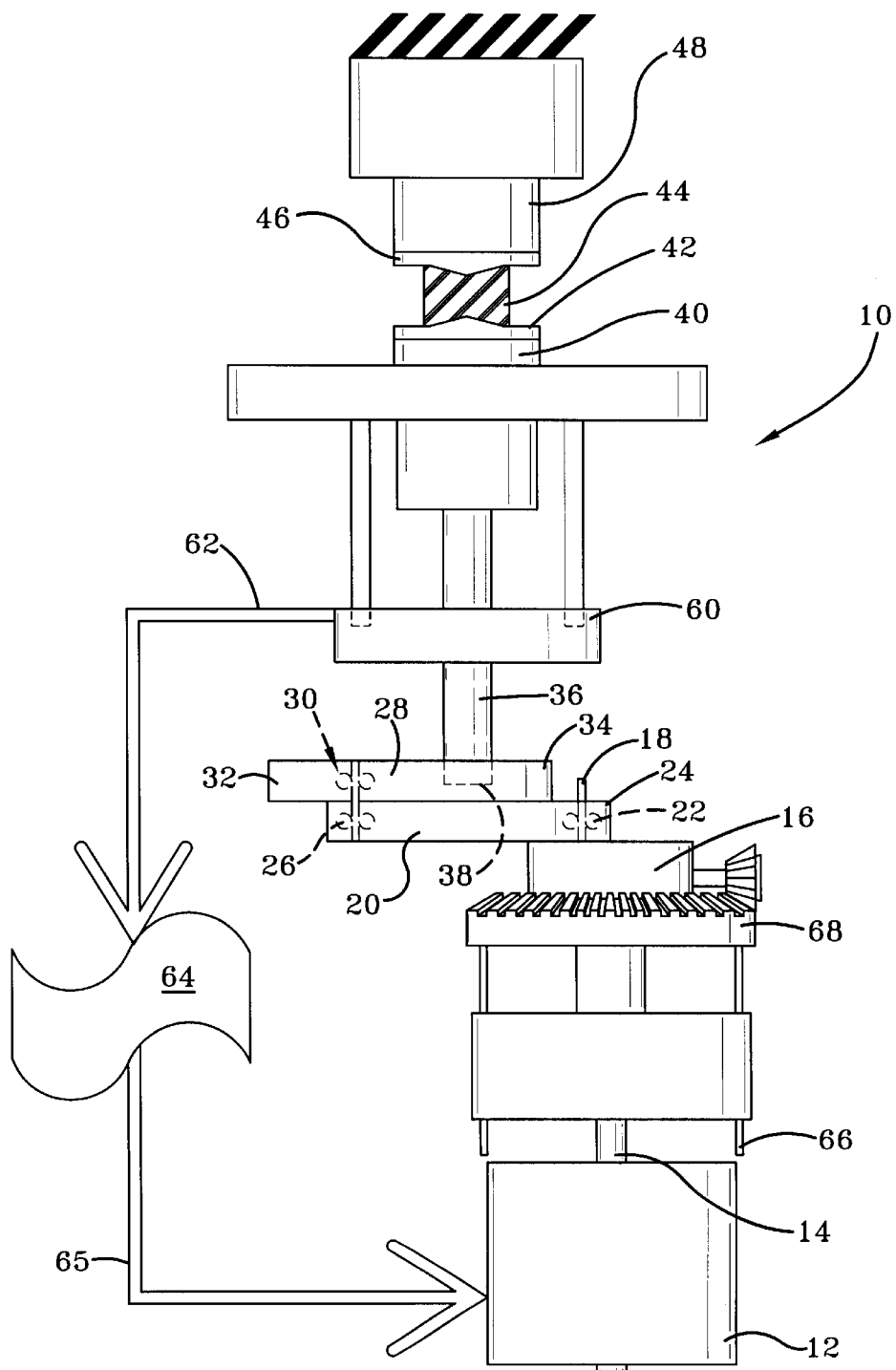
FIG. 4 is a schematic representation of a automatic variable eccentric rheometer system according to the present invention.

Referring now to FIG. 4, it can be seen that an automatic variable eccentric rheometer system according to this invention is designated generally by the numeral 10. Rheometer system 10 includes drive motor 12, which rotates drive shaft 14. Drive shaft 14 is rigidly fixed to eccentric cam 16, such that rotation of drive shaft 14 is directly transferred to eccentric cam 16. Eccentric cam 16 thus has a central axis of rotation running through the center thereof and through the center of drive shaft 14, and a connector 18 is operatively fixed to eccentric cam 16, off-set from this center axis of rotation. Connector 18 and its affixation to eccentric cam 16 will be discussed more fully below. Although connector 18 may take many functionally operative form, in the preferred embodiment herein, connector 18 is a pin that is operatively fixed to eccentric cam 16 and to eccentric arm 20. Connector 18, in such a preferred embodiment, connects to eccentric arm 20 through bearing 22, at first end 24 of eccentric arm 20. Second end 26 of eccentric arm 20 is attached to drive plate 28 through a pin and bearing assembly 30 associated with first end 32 of drive plate 28 and second end 26 of eccentric arm 20. Second end 34 of drive plate 28 is rigidly fixed to die shaft 36 at first end 38 thereof. Second end 40 of die shaft 36 is rigidly fixed to polymer sample die 42. Thus, rotation of drive shaft 14 by motor 12 causes rotation of eccentric cam 16, such that first end 24 of eccentric arm 20 rotates around the central axis of rotation of eccentric cam 20 to cause plate 28 to be pushed and pulled in an oscillating motion. This, in turn, causes the oscillation of polymer sample die 42.

In the complete mode of testing, then, a polymer specimen 44 is contained between polymer sample die 42 and stationary die 46. As polymer sample die 42 oscillates, torque transducer 48 measures the reaction torque that is the result of the resistance of the polymer specimen to the oscillatory motion. In addition, heating may be applied to the specimen, in conventional manners not shown here. The preferred test method as described by ASTM D6601 requires testing at increasing amplitudes of oscillation, and, thus, when employing rheometer system 10, a measurement would first be made at one amplitude of oscillation, and, thereafter, a change in the amplitude of oscillation would be made according to one of the methods described herein below in the further description of eccentric cam 16, and further measurements would be made. Additional measurements would be made at different amplitudes, until all measurements at different amplitudes are complete.

Figure 5:
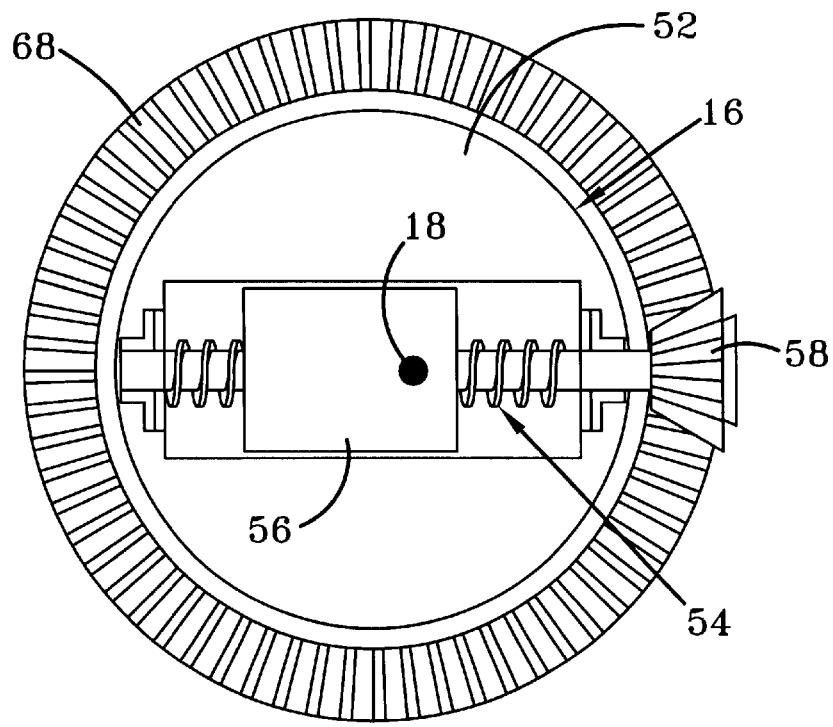
FIG. 5 is a top plan view of an automated variable eccentric cam and associated elements according to this invention.
Figure 6:
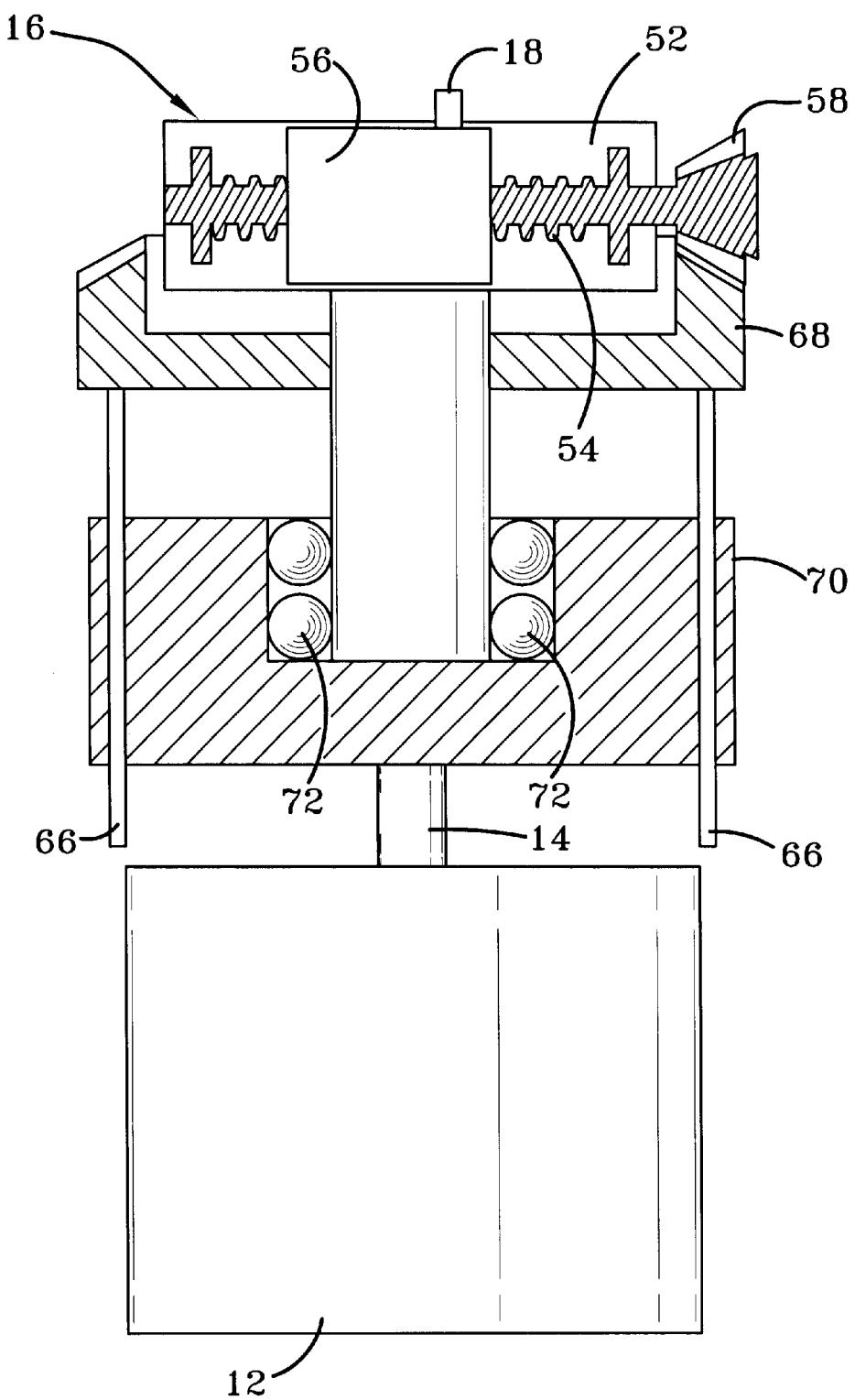
FIG. 6 is a side, cross-sectional view of the automated variable eccentric cam.

Referring now to FIGS. 5 and 6, eccentric cam 16 is more specifically disclosed. Particularly, further elements of eccentric cam 16 are identified, and the operation of eccentric cam 16 and elements associated therewith to achieve differing amplitudes of oscillation is disclosed. Eccentric cam 16 includes slide housing 52, which is fixed to drive shaft 14 to rotate therewith. As mentioned, eccentric cam 16 thus has a center axis of rotation. Slide screw 54 is mounted in slide housing 52, and slide 56 is threaded on slide screw 54. Connector 18 is mounted to slide 56. Rotation of slide screw 54 in either direction will cause slide 56 to move within its confines in slide housing 52, and rotation of slide screw 54 is achieved through rotation of bevel gear 58. Thus, the position at which pin 18 is off-set from the central axis of rotation of eccentric cam 16 can be set by rotation of bevel gear 58.

Referring additionally to FIG. 4, when rheometer system 10 is first initialized, the amplitude of oscillation is initially determined. Encoder 60 is attached to die shaft 36, such that movement of die shaft 36 results in an accurate pulse count from the encoder, which is output as an output signal designated herein as output signal 62. Processor 64 interprets output signal 62, and determines the amplitude of oscillation, in degrees, as motor 12 slowly rotates. If the amplitude of oscillation needs to be changed, processor 64 stops the rotation of motor 12 and emits an output signal 65 that signals bevel gear actuator 66 to raise engaging bevel gear 68 to mate with bevel gear 58. More particularly, as seen best in FIG. 6, engaging bevel gear 68 is mounted on bevel gear actuator 66, which is mounted in mounting plate 70. An air cylinder or solenoid or similar component in mounting plate 70 and associated with bevel gear actuator 66 may be employed to provide the mechanical means for raising or lowering actuator 66. Notably, mounting plate 70 includes eccentric bearings 72 that permit eccentric cam 16 to rotate therein. Once engaging bevel gear 68 has mated with bevel gear 58, processor 64 signals motor 12 to rotate slowly by emitting a different output signal 65. This rotation causes slide 56 to move, resulting in a change of amplitude of oscillation (due to the movement of connector 18 in relation to the central axis of rotation of eccentric cam 16). It will be readily appreciated that, if the current amplitude of oscillation, the pitch of slide screw 54, and the ratio of bevel gear 58 to engaging bevel gear 68 are known, the distance that motor 12 must turn in order to achieve a new, desired amplitude of oscillation can be readily calculated. When motor 12 has moved the required distance, processor 64 signals bevel gear actuator 66 to lower engaging bevel gear 68. Processor 64 then signals motor 12 to rotate slowly in order to verify that the desired amplitude of oscillation has been reached, by interpreting output signal 62. This provides a feedback to allow for further adjustments, if necessary.

Figure 7:
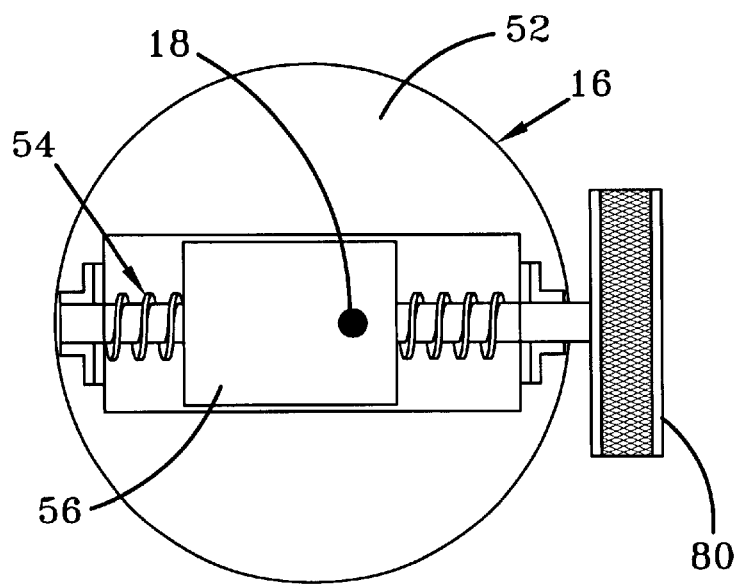
FIG. 7 is a top plan view of a manual variable eccentric cam according to this invention.

It should be appreciated that the present invention should not be limited to or by any specific means for adjusting the position of slide 56 within slide housing 52. Indeed, the present invention also contemplates a manual variable eccentric cam, which is shown in FIG. 7. Therein, like parts have received like numerals, and engaging bevel gear 68 and its associated elements are no longer present. Rather, bevel gear 58 is therein replaced with a manual adjusting nut 80. Manual adjusting nut 80, as its name implies, may simply be manually manipulated to move slide 56 within housing 52.

In light of the foregoing, it should thus be evident that the process of the present invention, providing a variable eccentric rheometer system, substantially improves the art. While, in accordance with the patent statutes, only the preferred embodiments of the present invention have been described in detail hereinabove, the present invention is not to be limited thereto or thereby. Rather, the scope of the invention shall include all modifications and variations that fall within the scope of the attached claims.

What is claimed is:

1. An eccentric cam for use in oscillating rheometer systems wherein the eccentric cam is mounted on a drive shaft and attaches to an eccentric arm for converting rotary motion of the drive shaft into oscillatory motion at a polymer specimen die, which is operatively connected to the eccentric arm through a die shaft and drive plate, the eccentric cam comprising:

a slide housing operatively connected to the drive shaft to rotate therewith such that said slide housing has a center axis of rotation;

a slide screw mounted in said slide housing;

a slide threaded on said slide screw and including a connector for attachment to the eccentric arm; and means for rotating said slide screw to move said slide and thereby change the position of said connector relative to the center axis of rotation of said slide housing.

2. The eccentric cam of claim 1, wherein said means for rotating said slide screw is a bevel gear.

3. The eccentric cam of claim 1, wherein said means for rotating said slide screw is a manually adjustable nut.

4. A variable eccentric rheometer system comprising:

a rotary drive shaft;

a slide housing operatively connected to said rotary drive shaft to rotate therewith such that said slide housing has a center axis of rotation;

a slide screw mounted in said slide housing;

a slide threaded on said slide screw and including a connector;

means for rotating said slide screw to move said slide and thereby change the position of said connector relative to the center axis of rotation of said slide housing;

an eccentric arm having a first end and a second end, said first end fixed to said connecter of said slide by a bearing, a drive plate having a first end and second end, said first end of said drive plate fixed to said second end of said eccentric arm;

a die shaft having a first end and a second end, said first end rigidly fixed to said second end of said drive plate;

a die rigidly fixed to said second end of said die shaft.

5. The variable eccentric rheometer system of claim 4, wherein said means for rotating said slide screw is a manually adjustable nut.

6. The variable eccentric rheometer system of claim 4, wherein said means for rotating said slide screw is a bevel gear.

7. The variable eccentric rheometer system of claim 6, further comprising:

a processor; and an encoder fixed around said die shaft to provide and output signal to said processor, said processor calculating an amplitude of oscillation of the die shaft.

8. The variable eccentric rheometer system of claim 7, further comprising:

a motor for rotating said drive shaft;

a mounting plate fixed around said drive shaft;

a bevel gear actuator mounted in said mounting plate; and an engaging bevel gear mounted on said bevel gear actuator.

\* \* \* \* \*